US012731684B2

(12) United States Patent
Becka et al.

(10) Patent No.: US 12,731,684 B2
(45) Date of Patent: Sep. 8, 2026

(54) METHOD AND SYSTEM FOR GENERATING A SOFTWARE-IMPLEMENTED MODULE FOR DETERMINING AN ANALYTE VALUE, COMPUTER PROGRAM PRODUCT, AND METHOD AND SYSTEM FOR DETERMINING AN ANALYTE VALUE

(71) Applicant: Roche Diabetes Care, Inc., Indianapolis, IN (US)

(72) Inventors: Larissa Becka, Munich (DE); Alexander Buesser, Zürich (CH); Tony Huschto, Speyer (DE); Yannick Klopfenstein, Neuchatel (CH); David Mesterhazy, Nuremberg (DE); Mike Rinderknecht, Zürich (CH); Christian Ringemann, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 38 days.

(21) Appl. No.: 18/057,060

(22) Filed: Nov. 18, 2022

(65) Prior Publication Data

US 2023/0092186 A1 Mar. 23, 2023

Related U.S. Application Data

(63) Continuation of application No. PCT/EP2021/063009, filed on May 17, 2021.

(30) Foreign Application Priority Data

May 19, 2020 (EP) .................................... 20175348

(51) Int. Cl.
*G16H 50/20* (2018.01)
*G06N 20/00* (2019.01)
(Continued)

(52) U.S. Cl.
CPC ............ *G16H 40/63* (2018.01); *G06N 20/00* (2019.01)

(58) Field of Classification Search
CPC ........ G16H 40/63; G16H 50/50; G16H 50/20; G06N 20/00; A61B 5/14532; A61B 5/746
See application file for complete search history.

(56) References Cited

U.S. PATENT DOCUMENTS

| | | | | |
|---|---|---|---|---|
| 11,568,992 | B2 * | 1/2023 | Jordan | G06N 3/084 |
| 2019/0133506 | A1 * | 5/2019 | Ringemann | A61B 5/746 |

(Continued)

OTHER PUBLICATIONS

International Search Report and Written Opinion of the International Searching Authority, PCT/EP2021/063009, Aug. 9, 2021, 14 pages.

(Continued)

*Primary Examiner* — Maroun P Kanaan
(74) *Attorney, Agent, or Firm* — Bose Mckinney & Evans LLP

(57) ABSTRACT

A method for generating a software-implemented module for determining a glucose value in a body fluid. A first set of input data indicative of first values measured for first and a second input parameters is provided. A second set of input data indicative of second values for the first and second input parameters is also provided. The first and second sets of input data are processed by a physiological model to determine first and second sets of glucose values, respectively, in a body fluid. Training data is determined and a set of test data different from the training data is also determined. A software-implemented machine learning model configured to determine a glucose value in a body fluid of a patient is provided and is trained by the training data and is tested by the test data.

15 Claims, 8 Drawing Sheets

(51) Int. Cl.
*G16H 10/20* (2018.01)
*G16H 40/63* (2018.01)

(56) References Cited

U.S. PATENT DOCUMENTS

| | | | | |
|---|---|---|---|---|
| 2019/0246973 | A1 | 8/2019 | Constantin et al. | |
| 2019/0252079 | A1 | 8/2019 | Constantin et al. | |
| 2021/0050085 | A1* | 2/2021 | Hayter | G16H 10/60 |
| 2021/0295515 | A1* | 9/2021 | Berg | G06T 5/50 |

OTHER PUBLICATIONS

Hidalgo et al., Glucose forecasting combining Markov chain based enrichment of data, random grammatical evolution and Bagging, Applied Soft Computing Journal, Nov. 14, 2019, vol. 88, No. 14, 12 pages.

Oviedo et al., A review of personalized blood glucose prediction strategies for T1DM patients, International Journal for Numerical Methods in Biomedical Engineering, Oct. 28, 2016, vol. 33, No. 6, 21 pages.

Contreras et al., Personalized blood glucose prediction: A hybrid approach using grammatical evolution and physiological models, PLoS One, Nov. 7, 2017, vol. 12, No. 11, 16 pages.

* cited by examiner

METHOD AND SYSTEM FOR GENERATING A SOFTWARE-IMPLEMENTED MODULE FOR DETERMINING AN ANALYTE VALUE, COMPUTER PROGRAM PRODUCT, AND METHOD AND SYSTEM FOR DETERMINING AN ANALYTE VALUE

RELATED APPLICATIONS

This application is a continuation of PCT/EP2021/063009, filed May 17, 2021, which claims priority to EP 20 175 348.0, filed May 19, 2020, both of which are hereby incorporated herein by reference.

BACKGROUND

The present disclosure refers to a method and a system for generating a software-implemented module for determining an analyte value, and a computer program product. Further, the present disclosure refers to a method and a system for determining an analyte value.

For predicting a glucose level of a patient different models to be applied in the prediction process have been proposed. On one hand, so-called physiological (glucose prediction) models have been proposed. Further, machine learning (glucose prediction) models which may also be referred to as data driven (glucose prediction) models have been applied.

It was found a difficult task to build a solely data driven glucose prediction model that is sensitive against, e.g., insulin or carbohydrate intakes, especially if the data for the model training does stem from real-world user data. Those datasets will only reflect a very narrow treatment region for an individual patient (most patients in most situations will handle their therapy well and fringe cases are rare). Any machine learning algorithm will therefore have difficulties to generalize the response towards insulin or carbohydrates outside of the normal treatment region of a particular patient. On the other hand, exactly the situations outside of the usual treatment region are cases where a glucose prediction algorithm would be most useful to a patient, either to warn against mistakes or by helping to find an optimal response to a critical situation. An example would be a recommendation about how much carbohydrate a patient should take in a situation of critical low glucose values to reach again the normal glucose concentration range.

For overcoming such shortcomings of a purely data driven model a hybrid approach was proposed whereby the glucose kinetics due to carbohydrate or insulin intakes are modelled by a physiological (first-principle) model. This may ensure sensitivity towards such inputs by design and provide a machine learning model that captures the residual effects on the glucose kinetics that are not well captured by the physiological model. Such an approach nevertheless has the disadvantage that two types of models in production have to be implemented and maintained, which is time consuming and costly.

The article Contreras et al. (2017), *Personalized blood glucose prediction: A hybrid approach using grammatical evolution and physiological models*, PLoS One 12 (11), pertains to a hybrid approach comprising physiological models for insulin and grammatical evolution, taking into account clinical harm caused by deviations from the target blood glucose by using a penalizing fitness function based on the Clarke error grid.

Oviedo et al. (2017), *A review of personalized blood glucose prediction strategies for T1DM patients*, International journal for numerical methods in biomedical engineering 33 (6), describes models for predicting blood glucose (BG) concentration, risks and BG events. The models are classified and the most relevant data regarding the experimental setup for fitting and testing each model as well as the input signals and the performance metrics are presented.

U.S. Publication No. 2019/0252079 A1 discloses the use of machine learning to determine a patient's physiological state and provide guidance to a patient regarding management of a physiologic condition such as diabetes.

Hidalgo et al., *Glucose forecasting combining Markov chain based enrichment of data, random grammatical evolution and Bagging*, Applied Soft Computing, 88, 2019 discloses a method for generating a software-implemented module for determining a glucose value. In the process of generating the software-implemented module, a machine learning process is applied. No physiological model is used. An enrichment of data is applied prior to the machine learning process.

SUMMARY

This disclosure teaches a method, a system, and a computer program product for generating a software-implemented module for determining an analyte value. Further, a method and a system for determining an analyte value are also disclosed.

According to an aspect, a method for generating a software-implemented module for determining an analyte value is provided. The method comprises, in an arrangement of one or more data processors, providing a first set of input data indicative of first values measured for a plurality of input parameters, the input parameters comprising a first and a second input parameter and providing a second set of input data indicative of second values for the plurality of input parameters. The second values comprise an augmented value for at least one input parameter from the plurality of input parameters, the augmented value being different from the first value measured for the at least one input parameter and determined by augmenting the first value, and the first value for at least one remaining input parameter from the plurality of input parameters. The method further comprises determining first analyte data indicative of a first plurality of analyte values for an analyte by processing the first set of input data by a physiological model; determining second analyte data indicative of a second plurality of analyte values for the analyte by processing the second set of input data by the physiological model; determining a set of training data from both the first analyte data and the second analyte data; determining a set of test data, the set of test data being different from the set of training data; providing a software-implemented machine learning model configured to determine an analyte value for the analyte; training the software-implemented machine learning model by the set of training data; and testing the software-implemented machine learning model by the set of test data.

According to another aspect, a system for generating a software-implemented module for determining an analyte value, comprising an arrangement of one or more data processors, is provided. The one or more processors are configured to provide a first set of input data indicative of first values measured for a plurality of input parameters, the input parameters comprising a first and a second input parameter and provide a second set of input data indicative of second values for the plurality of input parameters. The second values comprise an augmented value for at least one input parameter from the plurality of input parameters, the augmented value being different from the first value measured for the at least one input parameter and determined by augmenting the first value, and the first value for at least one remaining input parameter from the plurality of input parameters. The one or more processors are further configured to determine first analyte data indicative of a first plurality of analyte values for an analyte by processing the first set of input data by a physiological model; determine second analyte data indicative of a second plurality of analyte values for the analyte by processing the second set of input data by the physiological model; determine a set of training data from both the first analyte data and the second analyte data; determine a set of test data, the set of test data being different from the set of training data; provide a software-implemented machine learning model configured to determine an analyte value for the analyte; train the software-implemented machine learning model by the set of training data; and test the software-implemented machine learning model by the set of test data.

According to another aspect, a computer program product for generating a software-implemented module for determining an analyte value is provided. The computer program product comprises instructions which, when the program is executed on an arrangement of one or more data processors, cause the arrangement of the one or more data processors to carry out or conduct the method.

According to still another aspect, a method for determining an analyte value, the method comprising, in an arrangement of one or more data processors: providing the software-implemented module running in the arrangement of one or more data processors; providing present input data indicative of present values measured for a plurality of input parameters for a fluid containing an analyte; and determining an analyte value comprising analyzing the present input data by the software-implemented module.

According to a further aspect, a system for determining an analyte value is provided, the system having an arrangement of one or more data processors and a software-implemented module running in the arrangement of one or more data processors, wherein the one or more data processors are configured to provide present input data indicative of present values measured for a plurality of input parameters for a fluid containing an analyte; and determine an analyte value, comprising analyzing the present input data by the software-implemented module.

In an embodiment, the measurement data may be indicative of an analyte in a bodily fluid.

The system for determining an analyte value may, for example, be selected from the group consisting of a smart phone, a computer, a tablet, a receiver of a blood glucose meter or of a continuous glucose monitoring device, a remote control of a medication delivery pump and a medication delivery pump.

The analyte may be glucose in a sample of a bodily fluid, such as interstitial fluid or blood, in particular interstitial fluid. Measured values, for example the first values, may be (time-) continuously measured.

Different physiological models known as such may be applied for determining the first analyte data indicative of the first plurality of analyte values for the analyte by processing the first set of input data. Similarly, different data driven or machine learning models known as such may be applied in the technology disclosed.

At least one of the first input parameter and the second input parameter may be selected from the following group of input parameters: glucose level measured by continuous glucose measurement, insulin bolus carbohydrate intake, active bolus insulin, active basal insulin, activity level, insulin sensitivity factor, carbohydrate ratio, stress level, and glycemic index of carbohydrates.

The software-implemented module, after being generated, can be applied for determining an analyte value of the analyte, for example, for a sample containing the analyte. Measurement data gathered for one or more patients may be processed or analysed by the software-implemented module for determining the analyte value for the analyte. For example, measurement data from a continuous glucose monitoring (CGM) and/or blood glucose measurement (BGM) may be processed or analysed by the software-implemented module. The measurement data, optionally combined with additional data, provide for an input to the software-implemented module. The software-implemented module may be applied for predicting (determining a future value) an analyte value of the analyte, such as a glucose level of a patient.

The determining of the first analyte data may comprise determining first predictive analyte data indicative of a first time dependent course (trace) of the analyte values for the analyte over a prediction time period by processing the first set of input data by the physiological model. Additionally or alternatively, the determining of the second analyte data may comprise determining second predictive analyte data indicative of a second time dependent course of the analyte values for the analyte over the prediction time period by processing the second set of input data by the physiological model.

The first time dependent course of the analyte for the analyte and/or second time dependent course of the analyte values for the analyte may be a continuous glucose monitoring (CGM) trace. The prediction time period may start at a cutoff time. The prediction time period may have a length of 24 time buckets, alternatively 12 or 36 time buckets. Each time bucket can correspond to a same time interval of same length, e.g., 15 minutes, 10 minutes, or 5 minutes. Alternatively, the length can be variable.

Each time dependent course of the analyte values for the analyte over a prediction time period may be determined by Kalman prediction using a Kalman filter. The Kalman filter may be used to estimate an initial state of the system. The initial state of the system may comprise an analyte value, preferably a glucose value $x_0(t)=y_0(t)$ at time t=0. The initial state of the system may indicate the state of the system at time t=0. It may indicate how the system may evolve over time without carbohydrate intake or bolus insulin injection.

Alternatively, an autoregressive (AR) model may be used to estimate the initial state of the system.

Each time dependent course of the analyte values for the analyte over a prediction time period may be determined by hybrid prediction.

The providing of the first set of input data may comprise providing a first set of input data indicative of first values measured for the plurality of the input parameters over a measurement time period. In addition or alternatively, the providing of the second set of input data may comprise providing a second set of input data indicative of second values for the plurality of the input parameters over the measurement time period. Alternatively, the first set of input data or the second set of input data is provided over parts or sub-periods of the measurement time period.

The prediction time period may be provided as a continuation of the measurement time period.

Alternatively, the prediction time period may at least partially overlap with the measurement time period. In particular, the prediction time period may be within the measurement time period, preferably at the end of the measurement time period.

Limit data indicative of a parameter limit (parameter bound) for the at least one input parameter may be received. Augmenting of the first value for the at least one input parameter the parameter may be limited, preferably, via the limit data. Further, augmenting of the first values and/or the second values for the at least one input parameter the parameter may be limited via the limit data. The limit data may be indicative of physiological limits of the analyte and/or be personalized for a patient.

The limit data may comprise an upper bound and/or a lower bound for the first value, in particular, an interval. The interval may be a carbohydrate intake range, a bolus insulin range, or a CGM range, for example, [−600, 1000] mg/dl. The limit data may comprise a plurality of intervals. The limit data may also comprise a region for bounding pairs of values, for example, one or a plurality of sensitivity grid regions, preferably, the regions A, B, D, and E.

Determining of the set of test data may comprise determining a set of test data from the first analyte data only. Alternatively, determining of the set of test data may comprise determining the set of test data from the first analyte data and the second analyte data.

Alternatively, the set of test data may be determined from additional measured data and at least one of the first analyte data and the second analyte data. The additional measured data contain measured analyte data. Alternatively, the set of test data may be determined from the first analyte data and other measured data and, optionally, augmented analyte data. The measured data may, e.g., be determined via continuous glucose monitoring (CGM) and/or blood glucose meters (BGM).

The determining of the set of training data may comprise: determining residual analyte data; determining augmented analyte data from the second analyte data and the residual analyte data; and determining the set of training data at least from the augmented analyte data.

The determining of the residual analyte data may comprises residual analyte data from the first analyte data and measured analyte data. Analyte values of the residual analyte data may be determined from the first analyte data and the measured analyte data by subtracting, for example, for each corresponding time value, the analyte values of the first analyte data from analyte values of the measured analyte data. Analyte values of the augmented analyte data may be determined from the second analyte data and the residual analyte data by summating, for each corresponding time value, the analyte values of the second analyte data and the analyte values of the residual analyte data. It may be provided that the determined analyte values of the augmented analyte data are only accepted if they are within a predetermined range, in particular, a bounded interval, and otherwise rejected. The interval may, e.g., be [−600, 1000] mg/dl.

It may be provided that in case the determined analyte values of the augmented analyte data are rejected, the analyte values of the measured analyte data are stored as the analyte values of the augmented analyte data. It may be provided that a new augmented analyte data are determined until the determined analyte values of the augmented analyte data are accepted. The measured analyte data may be contained in the first set of input data or the first values. The measured analyte data may be a randomly extracted (data) sample.

In an embodiment, the augmented analyte data may represent an augmented CGM (continuous glucose monitoring) trace. CGM traces comprise measured CGM values. A physiologically simulated trace is determined using a physiological model. Simulation takes place for a simulation time period. Differences between the actual CGM values in the CGM trace and the CGM values in the simulated trace may be computed and stored in a residual CGM trace (residual analyte data). The residual CGM trace may be added to the augmented CGM trace.

Values for taken carbohydrates and/or bolus insulin may be replaced by an artificially (e.g., randomly) generated carbohydrate amount and/or bolus insulin amount. Based on the artificially generated values, a physiologically predicted artificial trace is determined using the physiological model. By adding the stored residual CGM trace to the physiologically predicted artificial trace, an augmented CGM trace (augmented analyte data) is determined. Characteristics of the original CGM trace such as bumps can appear again in the augmented CGM trace.

The set of training data may be determined including the measured analyte data.

It may be provided that a sensitivity value of the software-implemented machine learning model is adjusted by a ratio of amounts of augmented analyte data and non-augmented analyte data.

The providing of the first set of input data may comprise providing a first set of continuous input data indicative of first values continuously measured for a plurality of input parameters.

Additionally or alternatively, the providing of the second set of input data may comprise providing a second set of continuous input data indicative of second values continuously measured for a plurality of input parameters.

The method may further comprise providing a third set of input data indicative of third values for the plurality of input parameters, the third values comprising an augmented value for at least one other input parameter from the plurality of input parameters, the augmented value being different from the first value measured for the at least one other input parameter and determined by augmenting the first value; and the first value for at least one remaining input parameters from the plurality of input parameters. Further, the method may comprise determining third analyte data indicative of a third plurality of analyte values for the analyte by processing the third set of input data by the physiological model; and determining a set of training data from the first analyte data, the second analyte data, and the third analyte data. The set of test data may additionally be determined by the third analyte data.

The method may comprise providing a plurality of sets of input data, each indicative of values for the plurality of input parameters. It may be provided that for each set of input data, the respective values comprise an augmented value for at least one respective input parameter from the plurality of input parameters, and that each augmented value is different from the first value measured for the at least one respective input parameter and determined by augmenting the first value. The respective values may further comprise the first value for at least one remaining input parameters from the plurality of input parameters. It may be provided that respective analyte data indicative of a respective plurality of analyte values for the analyte is determined by processing the respective set of input data by the physiological model.

From the plurality of respective analyte data, a set of training data may be determined. The augmented values of the plurality of sets of input data may cover a range for one or more input parameters defined by input parameter limits, in particular, physiological parameter limits. The set of test data may additionally be determined by the respective analyte data.

It may be provided that the physiological model is not used as part of the prediction algorithm itself. It may rather be provided that the physiological model is used for expanding the training data with which the machine learning model is trained. In particular, a wider variety of physiologically meaningful data can be included in the training data. For example, glucose excursions spanning the full physiological spectrum may be included in the training data. A model that is trained on expanded training data may be able to better reflect expected physiological responses, e.g., towards carbohydrate or insulin inputs. Such a model may therefore be better suited to provide more physiologically meaningful glucose predictions, while at the same time retain high prediction accuracy.

The physiological model may provide a response from the input data. In particular, the physiological model may provide a glucose response from carbohydrate intake and/or bolus insulin injection. The process model may be described by the equation $y(t)=x_0(t)+f(u_1\, u_2, t)$, wherein $f$ is a transfer function, t denotes time, and $u_1$ and $u_2$ are functions representing carbohydrate intakes and bolus insulin injections, respectively.

The physiological model may also be described by the equation $Y(s)=K_1U_1(s)/((1+T_1s)^2s)+K_2\,U_2(s)/((1\,T_2s)^2s)$ or the equation $Y(s)=K_1U_1(s)/(1+T_1s)^2+K_2\,U_2\,(S)/(1\,T_2s)^2$, with glucose response Y as a function of the complex frequency number s, carbohydrate intakes $U_1$, bolus insulin injections $U_2$, and constants $K_1$, $K_2$, $T_1$ and $T_2$. The constants $K_1$ and $K_2$ may be related to an amplitude of glucose excursion after meal intakes and bolus insulin injection. The time constants $T_1$ and $T_2$ may determine the time for meal intakes/insulin injections to manifest themselves in a changed glucose value. The function Y may be the Laplace transform of the function y. In particular, the functions Y, $U_1$, $U_2$ of s in the Laplace domain may correspond to the functions y, $u_1$, $u_2$, respectively, in the time domain with variable t.

The physiological model may be patient-specific. The constants (model parameters) $K_1$, $K_2$, $T_1$ and $T_2$ may be determined by minimizing a cost function including measured data from a patient. The constants $K_1$, $K_2$, $T_1$ and $T_2$ may further be restricted to a physiologically meaningful range of values.

The second set of input data may provide for an artificial/synthetic set of input data derived (by augmentation) from the first set of input data. Augmenting a value may comprise artificially generating (e.g., randomly generating) another value and replacing the value with the other value. The random generation may adhere to a predetermined probability distribution. The artificially generated value may be limited to an interval. The augmented value may a carbohydrate intake value or a bolus insulin value.

The software-implemented machine learning model may be represented by a recurrent neural network, in particular, an encoder-decoder recurrent neural network. The software-implemented machine learning model may also be represented by other types of artificial neural networks.

The testing of the software-implemented machine learning model may be provided by determining accuracy values and/or sensitivity values towards bolus insulin and/or carbohydrates for the machine learning model.

Different physiological models known as such may be applied. In particular, at least one of the following models can be employed (see, for example, Oviedo et al. (2017), International journal for numerical methods in biomedical engineering 33 (6)): Lehmann and Deutsch glucose absorption model, modified Lehmann and Deutsch glucose absorption model, Berger plasma insulin concentration, Dalla Man glucose absorption model, Dalla Man insulin absorption model, Cobelli insulin model, Tarin's plasma insulin concentration model, Lehmann's glucose rate of appearance model, Dalla Man meal model, Verdonk plasma insulin model, autoregressive eXogenous (ARX) model, Berger's insulin kinetics model, Hovorka's meal absorption model, subcutaneous insulin absorption kinetics model, and time series models.

Similarly, different data driven or machine learning models known as such may be applied in the technology disclosed. For example, random forests, gradient boosting, self-organizing maps (SOM), and/or Jump NN can be employed.

With respect to the method for determining the analyte value, the method may further comprise at least one of: outputting the analyte value to a user through an output device; and if the analyte value is below a minimum threshold or above a maximum threshold, outputting an alarm to the user. If the analyte value to be determined is a glucose level in a bodily fluid, the alarm may indicate one of hypoglycaemia and hyperglycaemia. The output device may be configured to output at least one of audio data and video data to the user or patient.

If the analyte is glucose and the analyte value is a glucose concentration, then the minimum threshold may be 70 mg/dl, in an embodiment 60 mg/dl and in another embodiment 50 mg/dl.

If the analyte is glucose and the analyte value is a glucose concentration, then the maximum threshold may be 140 mg/dl, in an embodiment 160 mg/dl and in another embodiment 200 mg/dl.

The output device may for example be selected from the group consisting of a smart phone, a computer, a tablet, a receiver of a blood glucose meter or of a continuous glucose monitoring device, a remote control of a medication delivery pump and a medication delivery pump.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

In the following, further embodiments are described with reference to figures. In the figures show.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
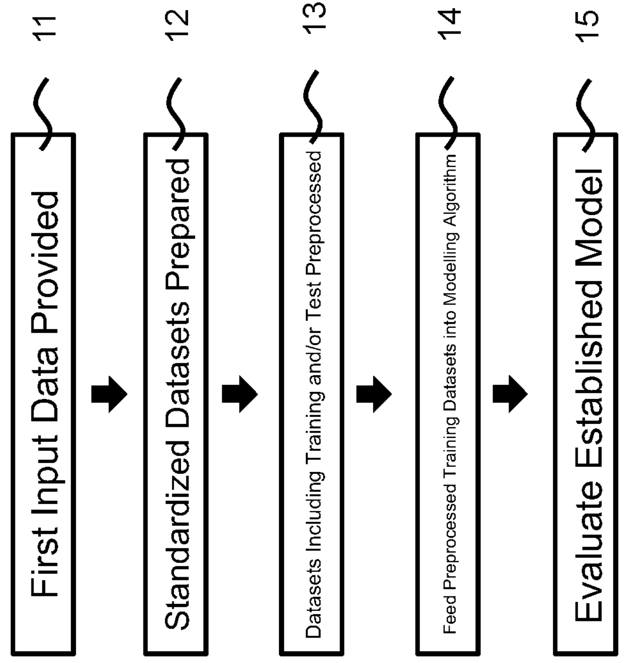
FIG. 1 is a graphical representation of a method for generating a software-implemented module for determining an analyte value.

FIG. 1 shows a graphical representation of a method for generating a software-implemented module for determining an analyte value.

In a step 11, sets of input data, in particular at least a first set of input data, are provided. The input data are indicative of values measured or determined for a plurality of input parameters. At least one of the sets of input data, for example the first set of input data, comprises raw data such as clinical study data. Out of the raw data, (standardized) datasets are prepared (step 12). This step may include partitioning the datasets into training and test datasets.

The input parameter may be selected from the following group of input parameters: glucose level measured for patients by continuous glucose measurement or monitoring (CGM), insulin bolus carbohydrate intake, active bolus insulin, active basal insulin, activity level, insulin sensitivity factor, carbohydrate ratio, stress level, and glycemic index of carbohydrates.

Subsequently, the datasets including the training and/or the test datasets are preprocessed (step 13). This step may include artificial data augmentation of the training datasets. Alternatively, partitioning the datasets into training and test datasets may also be carried out after preprocessing. In this case, it may be provided that non-augmented datasets are identified and only non-augmented datasets are assigned to the test partition.

In step 14, the preprocessed training datasets are fed into a modelling algorithm, which establishes a model for predicting an analyte value, e.g., a continuous glucose measurement (CGM) value. In step 15, the established model is evaluated on the test data sets by use of at least one metric.

For modelling purposes, for each of the sets of input data, the raw data may be mapped onto a standardized time grid with individual time buckets of a certain length (length of time), resulting in the standardized datasets.

Figure 2:
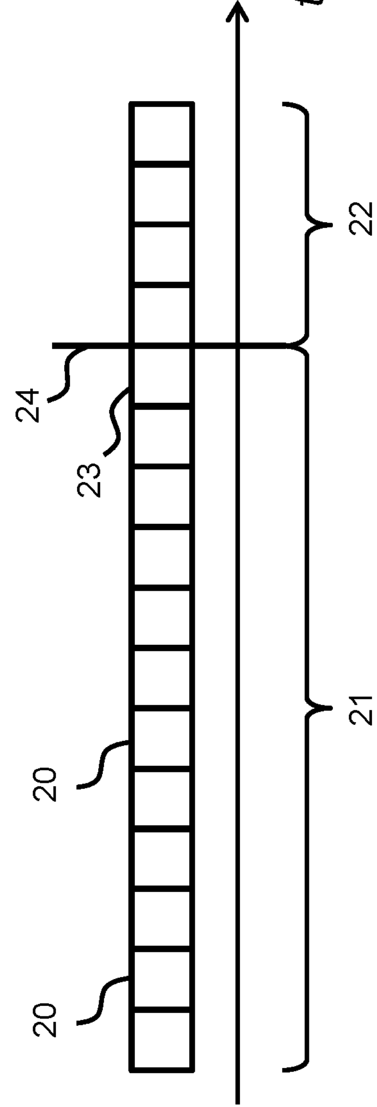
FIG. 2 is a graphical representation for allocating study data to time buckets.

FIG. 2 shows a graphical representation for allocating the study data to time buckets 20 along a time t axis. The length can be the same for each time bucket 20, e.g., 15 minutes, 10 minutes, or 5 minutes. Alternatively, the length can be variable.

The time horizon from which sequences of data are extracted (as, e.g., required for input to many-to-many sequence modelling) is represented by a feature extraction time window (FETW) 21. Note that in FIGS. 4 and 5, there is also measurement data in the prediction time period after cutoff time. It may be provided, however, that the measurement data in the prediction time period after the cutoff time is not employed for training. Further, a prediction time window (PTW) or prediction time period 22 represents the time horizon on which the model under consideration should yield a prediction.

The last time bucket (cutoff bucket) 23 for which data are available when a prediction is triggered is defined by a cutoff time 24.

The generated data are split into different partitions used for training (TRAIN) and testing (TEST). That is, for fixed FETW 21 and PTW 22, cutoff buckets are assigned either to the TRAIN or TEST partition.

Cutoffs in the TEST partition are defined without PTW 22 overlap. This allows for an unbiased assessment of generalization error when the machine learning models which also be referred to as predictive models are evaluated on the TEST set. For the TRAIN partition, no such requirement is imposed.

A patient-based TRAIN/TEST split is used, wherein all cutoff time buckets for patients are assigned at random either to the TRAIN or TEST partition.

In addition to defining the data split for training and testing of models, different scenarios are defined using predefined cutoff criteria (specific requirements in the vicinity of the cutoff). The criterion CARBOYDRATES_ALL represents carbohydrates taken in by a patient (in units of g). The criterion BOLUS_INSULIN represents bolus insulin in insulin units UI. These criteria are applied to the datasets in both the TRAIN and TEST partition.

General scenario:

FETW length=48 buckets, PTW length=24 buckets, no missing CGM values in FETW 21 and PTW 22, and—

CARBOYDRATES_ALL=0 and BOLUS_INSULIN=0 in PTW.

Postprandial scenario:

FETW length=48 buckets, PTW length=24 buckets, no missing CGM values in FETW 21 and PTW 22, CARBOYDRATES_ALL≤200 and BOLUS_INSULIN≤100 for all last 9 buckets, CARBOYDRATES_ALL≥10 and BOLUS_INSULIN≥0.1 for any of the last 9 buckets, and CARBOYDRATES_ALL=0 and BOLUS_INSULIN=0 in PTW.

Outliers in the CGM values can be removed. "No missing CGM values" means that there is no time gap, for which no CGM value exists. The scenarios are designed to cover different situations a patient might experience during the day. Evaluating individual models on these scenarios may give a better understanding of how they might perform in a specific setting.

Based on the available data, the following distribution of scenario cutoffs into different partitions was obtained:

| Scenario | Partition | Number of cutoffs |
|---|---|---|
| General | TRAIN | 1'210'727 |
| General | TEST | 15'630 |
| Postprandial | TRAIN | 104'929 |
| Postprandial | TEST | 2'744 |

For each of the available time buckets, different features are constructed. For each of the constructed features, values are imputed, which is done in a three-step procedure:

1. Linear interpolation for missing values if entries not missing for longer than 15 minutes (for a bucket length of 5 minutes, this corresponds to 3 buckets).
2. Replacing remaining values with the per-patient median, mean, etc. (if available),
3. Replacing remaining values with the cohort median, mean, etc.

For each scenario and TRAIN/TEST partition, 3-dimensional (standardized) datasets (samples*features*time) are generated.

Each of the datasets comprises input variables ($X_{train}$ for a TRAIN dataset, $X_{test}$ for a TEST dataset) and output variables ($y_{train}$ for a TRAIN dataset, $y_{test}$ for a TEST dataset). Each of the input variables $X_t$rain and $X_{test}$ may comprise the following features:

HBA1C
STILL_ACTIVE_BASAL_INSULIN,
BOLUS_INSULIN,
BOLUS_INSULIN STILL_ACTIVE,
BASAL_INSULIN,
CARBOHYDRATES_ALL,
CIR_BEST_ESTIMATE_G_PER_IU,
ISF_BEST_ESTIMATE_MG_PER_DL_IU,
CGM.

HBA1C denotes glycolized hemoglobine, STILL_ACTIVE_BASAL_INSULIN denotes an amount of insulin separated into basal and bolus insulin that is still active a specific time point based on past insulin injections, BOLUS_ INSULIN denotes bolus insulin (in insulin units IU), CARBOHYDRATES_ALL denotes carbohydrates taken in by a patient (in units of g), CIR_BEST_ESTIMATE__G_PER_IU_denotes an estimated carbohydrate-to-insulin ratio, ISF_BEST_ESTIMATE_MG_PER_DL_IU denotes an estimated insulin sensitivity, and CGM denotes continuous glucose measurements (mg/dl).

The input variables $X_{train}$ and $X_{test}$ may further comprise the FETW length value (preferably 48 buckets).

Each of the output variables $y_{train}$ and $y_{test}$ may comprise the target variable (target) CGM for a subsequent modelling/learning algorithm and the PTW length value (preferably 24 buckets).

Dataset Preprocessing

In a “data driven with data augmentation” (DDwDA) approach, the TRAIN datasets are further preprocessed. Here, preprocessing is defined as any nontrivial modification of the TRAIN datasets that is expected to yield improved performance of data-driven predictive models on a separate evaluation (TEST) dataset.

In particular, data-driven sequence models for glucose prediction have so far failed to be sensitive towards carbohydrates and/or bolus insulin. Data preprocessing may help to improve this situation, independent of model type, architecture, and choice of hyperparameters.

The quality of any data-driven model is determined by the underlying training and test data. If the distribution of test data has little or no overlap with the training data, then the trained model will in general hardly be of any use for the target application. For example, a highly controlled clinical trial might miss to reflect the real-world. The goal of data augmentation is to improve model performance (as measured, e.g., by prediction accuracy or root mean square error, RMSE) or sensitivity towards specific features by modifying the training set.

Data augmentation methods can be described as a sequence of two distinct data preprocessing steps:

oversampling of a given dataset and
modification of samples or addition of modified samples in the (training) datasets DS (synthetic data generation).

The oversampling step is not strictly necessary in that any engine that generates synthetic examples from realistic data is sufficient for the purposes of data augmentation.

At least one of the TEST datasets is augmented by use of a physiological model (process model) which describes the glucose response Y in the Laplace domain (i.e., the Laplace transform of the glucose/CGM response y) after carbohydrate intakes $U_1$ or bolus insulin injection $U_2$ in the Laplace domain, respectively. Additionally or alternatively, at least one of the TRAIN datasets may be augmented by use of the physiological model (see FIGS. 4 and 5 below).

One of two physiological models PM1 or PM2 can be employed. The physiological model PM1 for the glucose response Y after carbohydrate intake $U_1$ or bolus insulin injection $U_2$ can be described by the following equation in the Laplace domain:

$$Y_{PM1}(s) = \frac{K_1}{(1+T_1 s)^2 \cdot s} \cdot U_1(s) + \frac{K_2}{(1+T_2 s)^2 \cdot s} \cdot U_2(s) \quad \text{(Eq. 1)}$$

The physiological model PM2 can be described by the following equation:

$$Y_{PM2}(s) = \frac{K_1}{(1+T_1 s)^2} \cdot U_1(s) + \frac{K_2}{(1+T_2 s)^2} \cdot U_2(s) \quad \text{(Eq. 2)}$$

Basal insulin injections are not considered in both physiological models. The physiological models PM1 and PM2 are similar. However, both transfer functions of the PM1 model include an additional integrator term that results in integrating behaviour. Whereas the PM2 model always returns to the stable equilibrium point of the model (the basal glucose state) after the effect of inputs has faded, this is not the case for the PM1 model, which does not have an equilibrium point. In the PM1 model, carbohydrate and insulin inputs have a persistent effect on the glucose level, which is caused specifically by the integrator term (pole at s=0).

Both model structures have the advantage that the model parameters have a direct physiological meaning. The constants $K_1$ and $K_2$ are related to the amplitude of the glucose excursion after meal intakes and bolus insulin injection, whereas the time constants $T_1$ and $T_2$ determine the time for meal intakes/insulin injections to manifest themselves in a changed glucose value. For the PM1 model, it was shown that the model parameters are useful estimates for the patient and mealtime specific carbohydrate-to-insulin ratio (CIR) and insulin sensitivity factor (ISF), which are used by T1D patients to compute their bolus insulin needs. In this case, the constant $K_2$ has the same physiological meaning as the factor ISF, whereas the physiological interpretation of the mixed constant $K_2/K_1$ is identical to that of CIR.

Identification of a patient specific model corresponds to the minimization of the following cost function $$J(\theta) = \sum_{d=1}^{d_{tot}} \left( \sum_{k=k_0(d)}^{k_N(d)} f\big(y_k - \hat{y}_k(\theta(d))\big)^2 \right) + \lambda_{reg} \frac{\hat{\sigma}_\theta^2}{\hat{\mu}_\theta^2}, \quad \text{(Eq. 3)}$$

wherein $$f\big(y_k - \hat{y}_k(\theta(d))\big) = \begin{cases} y_k - \hat{y}_k(\theta(d)) & \text{if } y_k < 100 \text{ mg/dl} \\ 100 \cdot \dfrac{y_k - \hat{y}_k(\theta(d))}{y_k} & \text{if } y_k \geq 100 \text{ mg/dl} \end{cases}. \quad \text{(Eq. 4)}$$

Alternatively, the function ƒ can be defined as ƒ $(\hat{y}_k - \hat{y}_k(\theta(d))) = y_k - \hat{y}_k(\theta(d))$ for any value of $y_k$. In the cost function, $y_k$ corresponds to the measured output, i.e., the CGM data, whereas $\hat{y}_k$ is the model output. Each data segment d ($d_{tot}$ in total) used in the identification segment is characterized by a starting index $k_0$ and an end index $k_N$. The model output $\hat{y}_k$ is computed using model parameters $\theta = (K_1, T_1, K_2, T_2)$ and an estimate of the initial state $\hat{x}_0$. The initial state estimate $\hat{x}_0$ corresponds to the state of the system at the start of the identification segment $k_0$. It may for example be provided that $\hat{x}_0=\hat{y}_0$. Regarding the parameter vector θ, for each data segment of a patient, the same parameter vector θ is used. Alternatively, a specific parameter vector θ for each segment can be employed.

When using a specific parameter vector θ for each segment, it is necessary to introduce a regularization term in order to prevent overfitting. This regularization term corresponds to the coefficient of variation (standard deviation divided by mean) of the parameter vectors θ for all data segments d. The importance of the term is determined by the parameter $\lambda_{reg}$. With this regularization term, each of the four parameters has the same weight, i.e., $$\frac{\hat{\sigma}_\theta}{\hat{\mu}_\theta} = \frac{\hat{\sigma}_{K_1}}{\hat{\mu}_{K_1}} + \frac{\hat{\sigma}_{T_1}}{\hat{\mu}_{T_1}} + \frac{\hat{\sigma}_{K_2}}{\hat{\mu}_{K_2}} + \frac{\hat{\sigma}_{T_2}}{\hat{\mu}_{T_2}}. \quad \text{(Eq. 5)}$$

In contrast, when using the same parameter vector to describe all identification data segments, this regularization term vanishes.

For identifying the model parameter $\theta=(K_1, T_1, K_2, T_2)$, the cost function J can be minimized, e.g., via the MATLAB routine FMINCON. In order to obtain not only good prediction results, but also sensible model parameters, the values of $K_1$, $T_1$, $K_2$, and $T_2$ are restricted in the optimization via FMINCON to a physiologically meaningful range. Two different settings can be employed, a wider and a narrower range for the parameter values. These, as well as the initial guess for parameter vector θ, are summarized as follows.

| | | PM1 | | PM2 | |
|---|---|---|---|---|---|
| | | narrow | wide | narrow | wide |
| K1 (mg/dl/g) | lower bound | 0.5 | 0.1 | 100 | 10 |
| | upper bound | 10 | 100 | 6000 | 60000 |
| | initial guess | CIR/ISF | | 100 · e · ISF/CIR | |
| T1 (min) | lower bound | 10 | 0.1 | 20 | 2 |
| | upper bound | 60 | 600 | 200 | 2000 |
| | initial guess | 29.5 | | 100 | |
| K2 (mg/dl/IU) | lower bound | −100 | −10000 | −80000 | −80000 |
| | upper bound | −10 | −0.1 | −1300 | −130 |
| | initial guess | −ISF | | −180 · e · ISF | |
| T2 (min) | lower bound | 25 | 0.25 | 50 | 5 |
| | upper bound | 250 | 2500 | 300 | 3000 |
| | initial guess | 56.7 | | 180 | |

state estimation 6 hours before the starting point of the identification data segment and computes estimates for the state for each of those time points up to the start of the identification segment. The last estimate of $\hat{x}$ (just at the start of the identification data segment) corresponds to the initial state for the system identification. The model inside the Kalman filter (derived from the process model with parameters θ) is updated in every iteration step of the optimization using the current guess of the model parameters θ, i.e., the process model for prediction and the (same) process model used for the Kalman filter are optimized simultaneously.

The fine tuning of the Kalman filter (which computes the state estimate $\hat{x}$ for each time step based on meal carbohydrates and bolus insulin, as well as on measured CGM data) determines how much the filter trusts the model for estimating state $\hat{x}$ and how much emphasis is put on the new CGM measurements that become available in each time step. This is done via the matrices Q and R. In case the values of Q are much larger than the values of R, the model is deemed not very trustworthy and the updating of the state estimate is mainly done based on the new CGM data. If however the values of R are much larger than the values of Q, not much emphasis is put on the CGM data and the updating is determined almost entirely by the model.

Diagonal matrices have been used for Q and R with diagonal entries q and r, respectively. The values of q and r can either be manually fine-tuned or treated as degrees of freedom for the optimization problem. In the latter case, in addition to the model parameters, q and r are also optimized in order to minimize the cost function J.

In case of putting a strong emphasis on the model inside the Kalman filter (r >>q), larger deviations between the filtered output at the initial state $\hat{y}_0$ and the CGM data at the same point in time can arise, which can be undesirable. In order to compensate for this effect, the difference between $\hat{y}_0$ from the Kalman filter and the CGM measurement at the same point in time can be computed and the model output $\hat{y}_k$ for the entire identification period is then shifted by this difference.

The following settings were employed for Kalman state estimation:

| Setting | $\hat{x}_0$ estimation | r | q (PM1) | q (PM2) | Optimize q and r | Compute Difference Between $\hat{y}_0$ and CGM Measurement | Constraints |
|---|---|---|---|---|---|---|---|
| A | false | — | — | — | — | true | narrow |
| B | true | $10^{10}$ | 30 | $3 \cdot 10^6$ | — | true | narrow |
| C | true | 10 | 0.1 | 0.1 | — | false | wide |
| C13 | true | $10^{10}$ | 30 | $3 \cdot 10^6$ | r | true | narrow |

Regarding the estimate 2 for the initial state of the system at the beginning of an identification data segment, three different methods can be employed:

Kalman state estimation, no state estimation, or hybrid state estimation.

For Kalman state estimation, a Kalman filter is used to estimate the initial state of the system using model inputs and available CGM measurements. The filter starts with its Preferably, the setting C13 is employed.

When alternatively using no state estimation, the system is assumed to be at a stable equilibrium state at the start of an identification data segment. This corresponds to $\hat{x}_0=0$, i.e., no impact of the initial state on the model output. For this method, the output of the physiological models PM1 and PM2 corresponds to 0 mg/dl in the absence of meals. The postprandial trajectories simulated as part of the identification procedure would therefore always start at 0 mg/dl. In order to still obtain sensible model outputs and identification results, it is assumed that the system is at a stable equilibrium state at the start of each identification data segment. This is a rather crude assumption that is probably the best fulfilled at breakfast, but less so for identification segments at lunch and dinner.

corresponds to the sum over all quadratic differences for all parameter vectors (plus an additional regularization term, see Eq. 3).

The following settings were employed for Bayesian state estimation. Preferably, narrow constraints (alternatively: wide constraints) are employed.

| Setting | $\hat{x}_0$ estimation | r | q (PM1) | q (PM2) | Optimize q and r | Compute Difference Between $\hat{y}_0$ and CGM Measurement | $\lambda_{prior}$ |
|---|---|---|---|---|---|---|---|
| F1 | true | 5000 | 0.1 | 0.1 | — | true | 0 |
| F3 | true | 5000 | 0.1 | 0.1 | — | true | 100 |
| F4 | true | 5000 | 0.1 | 0.1 | — | true | 1000 |
| F5 | true | 5000 | 0.1 | 0.1 | — | true | 10000 |

With regard to hybrid state estimation, $\hat{x}_0$ is assumed to be 0 for the process model. This means no impact of the initial state on the process model output. The effect of the initial state is captured by an autoregressive (AR) model. The predicted glucose output of this hybrid model then corresponds to the sum of the process model prediction and the prediction by the AR model. In this method, is not required to assume that the system is at a stable equilibrium state at the start of each identification data segment since the combined model output directly starts at the last measurement because of the AR model, whereas the process model is just used to describe the additional effects of meal and bolus insulin inputs. In this case, no Kalman filter is needed for the system identification (again, assuming $\hat{x}_0=0$ for the process model), but the fine-tuning of the AR model has of course an impact on the identification results and the predictive performance of the hybrid model.

Separate model parameters are determined for different times of the day, i.e., for any analyzed case always three models are generated:

Breakfast model: Only identification data segments with a starting time between 5:30 and 10:30 are considered in the system identification.

Lunch model: Only identification data segments with a starting time between 10:30 and 14:30 are considered in the system identification.

Dinner model: Only identification data segments with a starting time between 17:00 and 21:00 are considered in the system identification.

Apart from Kalman state estimation, no state estimation, or hybrid state estimation, a Bayesian approach for system identification can be employed. In this case, the cost function J in Eq. 3 contains an additional term that penalizes the difference between the identified model parameters and a predefined prior. In the case of using the same parameter vector to model all identification data segments, the modified cost function takes the following form:

$$J(\theta) = \sum_{d=1}^{d_{tot}} \left( \sum_{k=k_0(d)}^{k_N(d)} f\left(y_k - \hat{y}_k(\theta)\right)^2 \right) + \lambda_{prior}(\theta - \theta_{prior})^T \cdot (\theta - \theta_{prior}), \quad \text{(Eq. 6)}$$

wherein the function $f$ is defined as in Eq. 4 above. The second term in the cost function penalizes the quadratic difference between the identified parameter vector and a prior with a relative weight $\lambda_{prior}$. In case a different parameter vector is used for each data segment, this term With the physiological model established, predicted glucose trajectories can be computed as follows. Different horizons for prediction can be investigated. The data has a sample time $T_s$=5 min and predictions for horizons of k=1 (5 min) up to k=24 (120 min) are performed. Predictions are always performed on the complete dataset of each patient and for all different identified parameter sets (i.e., breakfast parameters, lunch parameters and dinner parameters). If meal-specific parameters are identified, the mean values over all meals are used for estimating the state $\hat{x}(t)$ of each process model as well as for doing predictions by simulating the process models based on this estimated state.

Two different prediction methods can be employed:

Kalman prediction (used with Kalman state estimation and no state estimation) and hybrid prediction (used with hybrid state estimation).

In the case of Kalman prediction, the identified parameters of the process model and the values of q and r are used to make state estimates of the process models $\hat{x}(t)$ at each time t based on input ($u_1$, $u_2$) (carbohydrate intakes $u_1$ and bolus insulin injection $u_2$) and output ($\Delta y=y-G_b$) data up to time t. $G_b$ denotes the patient's basal glucose over all identification days, i.e., the CGM mean value computed from the first 28 days of data of a patient.

Based on the signal of the estimated state $\hat{x}(t)$ for each point in time t, this state is used as initial condition for a simulation with the process model: $x_0=x(t)$. For the simulation, all future inputs (after the current time t) are removed (set to 0) and the output $Y_{sim,k}(t)$ is simulated for k=0, . . . , 24 steps. This way, the prediction of time t+k $T_s$, i.e., $$\hat{y}(t + k \cdot T_S | t) = y_{sim,k}(t) + G_b \quad \text{(Eq. 7)}$$

is computed. In case the difference between $\hat{y}_0$ from the Kalman filter and the CGM measurement at the same point in time is computed and the model output $\hat{y}_k$ for the entire identification period is shifted by this difference, the prediction is given by $$\hat{y}(t + k \cdot T_S | t) = y_{sim,k}(t) - y_{sim,0}(t) + y(t), \quad \text{(Eq. 8)}$$

wherein y(t) denotes the actual CGM measurement at time t.

In the case of hybrid prediction, the prediction is computed by $$\hat{y}(t+k\cdot T_S|t) = y_{sim,k}(t) + \hat{y}_{AR}(t+k\cdot T_S|t), \qquad \text{(Eq. 9)}$$

wherein $\hat{y}_{AR}$(t+k $T_s$ It) denotes the prediction of time k·$T_s$, given information up to time t, with a global AR model. As initial condition for $y_{sim,k}(t)$, $x_0=0$ is assumed.

A (second order) global AR model takes the form $$\Delta\hat{y}(t+k\cdot T_S) = a_k\Delta y(t) + b_k\Delta y(t-T_S), \qquad \text{(Eq. 10)}$$

$$\Delta y(t) = y(t) - G_b,$$

$$\hat{y}(t+k\cdot T_S) = \Delta\hat{y}(t+k\cdot T_S) + G_b,$$

where $G_b$ is the patient-specific basal glucose (mean CGM value over the first 28 days of each patient). The parameters ($a_k$, $b_k$) are optimized using least squares (LS) optimization for each prediction horizon $k \in \{1, 2, \ldots, 24\}$. The global AR model is identified on the first 28 days of data of all 175 patients in the training dataset combined.

Different variants of the global AR model can be employed:

a) Using all data (first 28 days of data of all 175 patients in the training dataset combined), b) Using all data without considering data segments where a prediction over a non-zero input is made, c) Same b), but instead of using the prediction error e(t)=Δŷ(t+kTs)−Δy(t) and using ordinary least squares LS $$\left(\text{i.e., } J(a_k, b_k) = \sum_{t=t_0}^{t_{tot}} e(t)^2\right),$$

the normalized error $$e(t) = \begin{cases} \Delta y(t) - \Delta\hat{y}(t+k\cdot T_S) & \text{if } y(t) < 100 \text{ mg/dl} \\ 100\cdot\dfrac{\Delta y(t) - \Delta\hat{y}(t+k\cdot T_S)}{y(t)} & \text{if } y(t) \geq 100 \text{ mg/dl} \end{cases}$$

is employed, resulting in a weighted least squares (WLS) problem.

d) Same as c), but only the data during the night (defined as between 23:00 and 5:30) are used.

As an alternative to the AR model, the prediction ŷ at time t+k·$T_s$ is computed via a zero order hold (ZOH) model based on the CGM data y up to time t by keeping the latest available value constant, i.e., ŷ(t+k·$T_s$)=y(t).

Using the physiological models and supplementary data for individual patients ($K_1$, $T_1$, $K_2$, $T_2$ . . . ), the following knowledge-driven data augmentation algorithm for augmenting CGM traces (time series of CGM values) is employed.

1. Define data augmentation parameters:

| Parameter | Description | Default Value |
|---|---|---|
| multiplication_factor | Fraction of data that needs to be augmented, e.g., 10%. | — |
| processed_or_raw_ system_variables | System variables to be used by the physiological model as input | raw |

-continued

1. Define data augmentation parameters:

| Parameter | Description | Default Value |
|---|---|---|
| max_carbohydrates | Maximum carbohydrate amount. Artificial carbohydrates will be in the interval [0, max_carbohydrates] | 250 g |
| max_bolus_insulin | Maximum insulin amount. Artificial bolus insulin will be in the interval [0, max_bolus_insulin] | 40 IU |
| ]min_cgm, max_cgm[ | CGM range. Range to be considered for a valid augmentation. Artificial CGM will be in the interval [min_cgm, max_cgm]. | [−600, 1000] mg/dl |
| mtw | Mealtime window length. Time window before cutoff to be considered to identify carb./insulin event | 45 minutes |
| replace_original_data | Are original data replaced by augmented traces? If false, augmented traces are added to the original data. | false |
| only_augment_ samples_with_event_ at_cutoff | Only augment traces for which there is an event (carbohydrates or bolus injection) at cutoff time. | true |
| augmentation_in_ ACDE | Only generate artificial inputs (carbohydrates and bolus) in the ACDE region of a predefined sensitivity grid. | true |

2. Extract random samples to be augmented based on data augmentation parameters.

3. For each extracted sample to be augmented:

a) Identify last entry bucket (of either input feature CARBOHYDRATES_ALL or BOLUS_INSULIN) in mealtime window MTW.

b) Calculate difference between actual CGM values and those of the physiological model (preferably C13) calculated at the last entry bucket in the mealtime window MTW and store this in a residual CGM trace CGM_DELTA.

c) At last entry bucket, replace CARBOHYDRATES_ALL and BOLUS_INSULIN with artificially generated carbohydrate and bolus insulin amounts.

d) Trigger prediction of physiological model with modified input data at time of last input until end of prediction time window (=CGM_PHYS).

e) Accept modified CGM trace (CGM_AUGMENTED=CGM_PHYS+CGM_DELTA) if signal is within bounds (see parameter CGM range [min_cgm, max_cgm] above), otherwise reject and store original CGM trace.

f) Repeat.

Alternatively or additionally, other types of values that can be predicted with a physiological model may be augmented. For example, values representing a degree of sport activity may be augmented.

Figure 3:
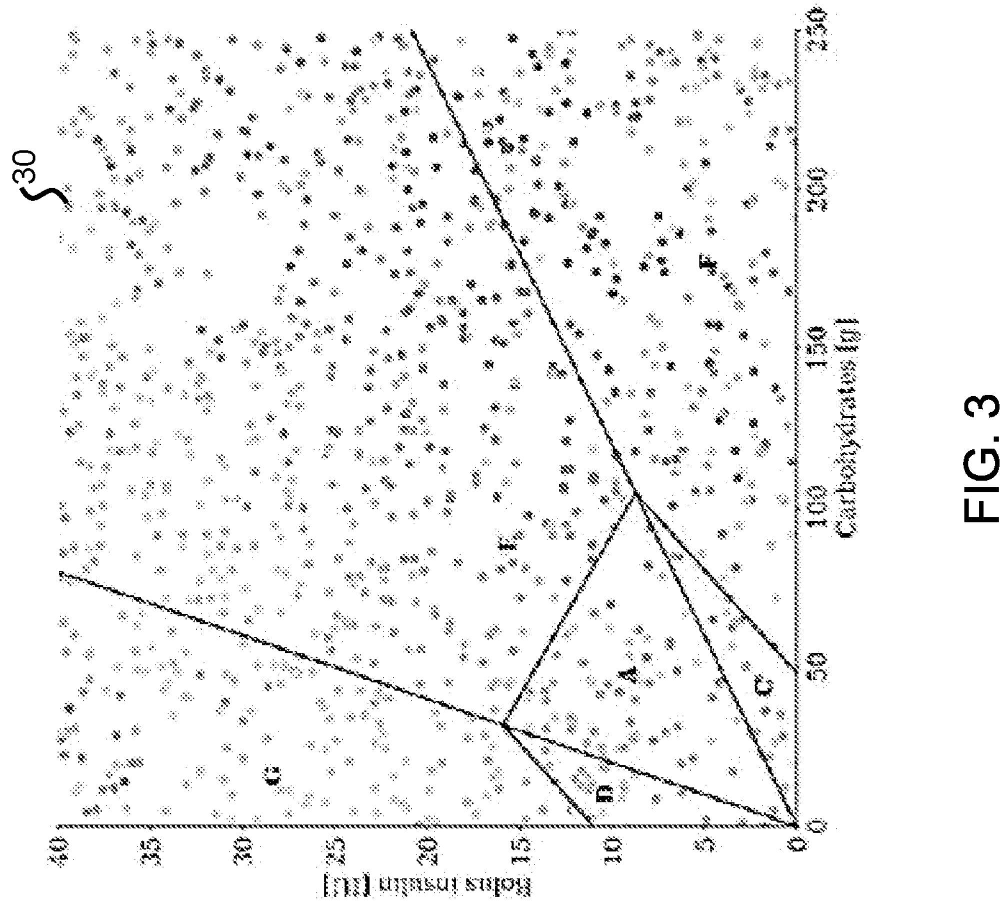
FIG. 3 is a graphical representation of a sensitivity grid.

FIG. 3 shows a graphical representation of a sensitivity grid. The sensitivity grid is partitioned in A, C, D, E, F, and G regions. Further, exemplary data points 30 corresponding to pairs of carbohydrates and bolus insulin are shown. The data points 30 represent an example of a distribution of carbohydrate and insulin values after augmentation.

Not all of the data points 30 are used for sensitivity calculation. Only pairs of carbohydrates and bolus insulin that are located in the regions A, C, D, and E of the sensitivity grid are acceptable. Data points 30 that are further away from the diagonal (not shown) represent more extreme cases.

Figure 4:
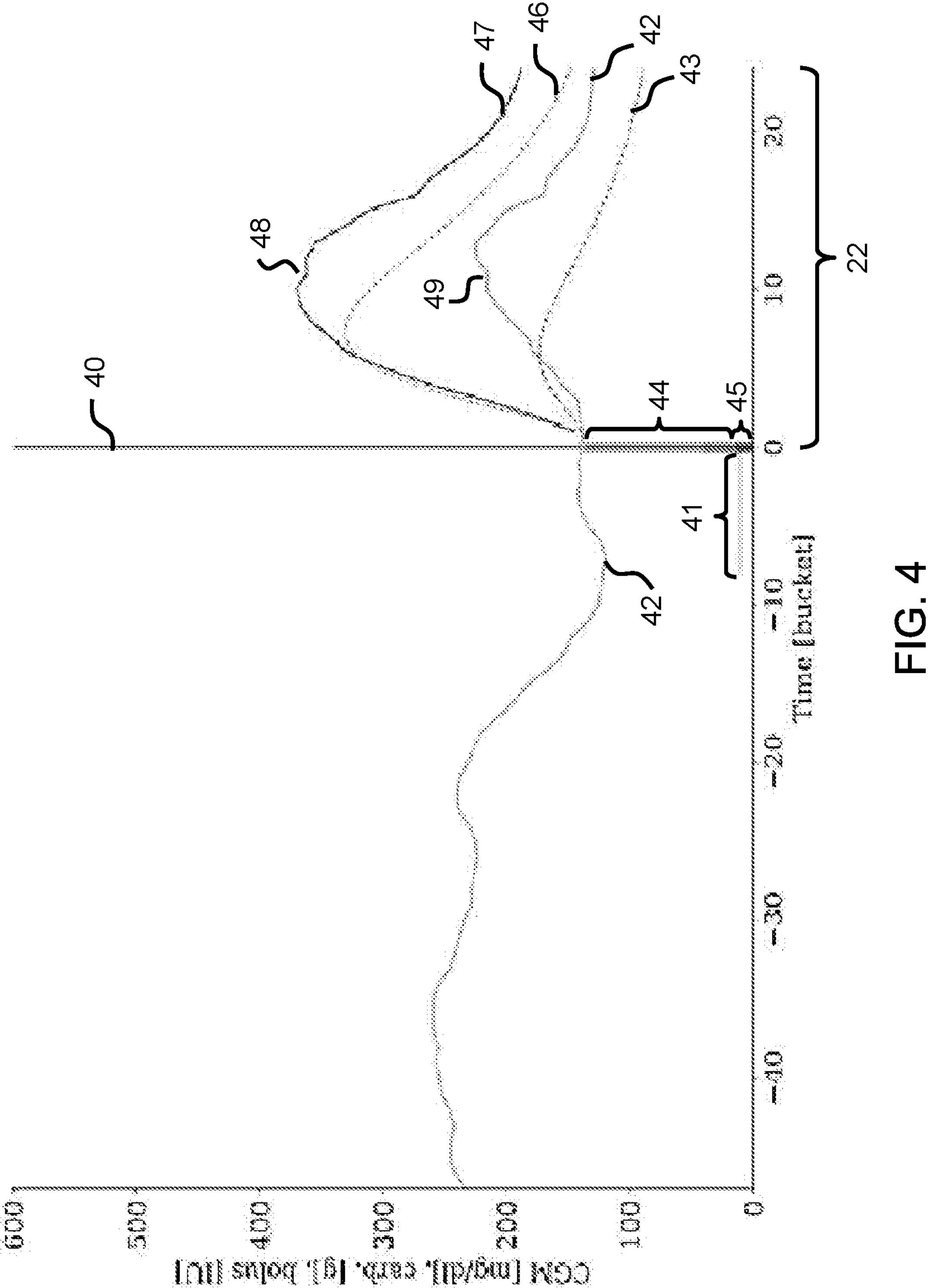
FIG. 4 is a graphical representation for generating an augmented CGM trace.
Figure 5:
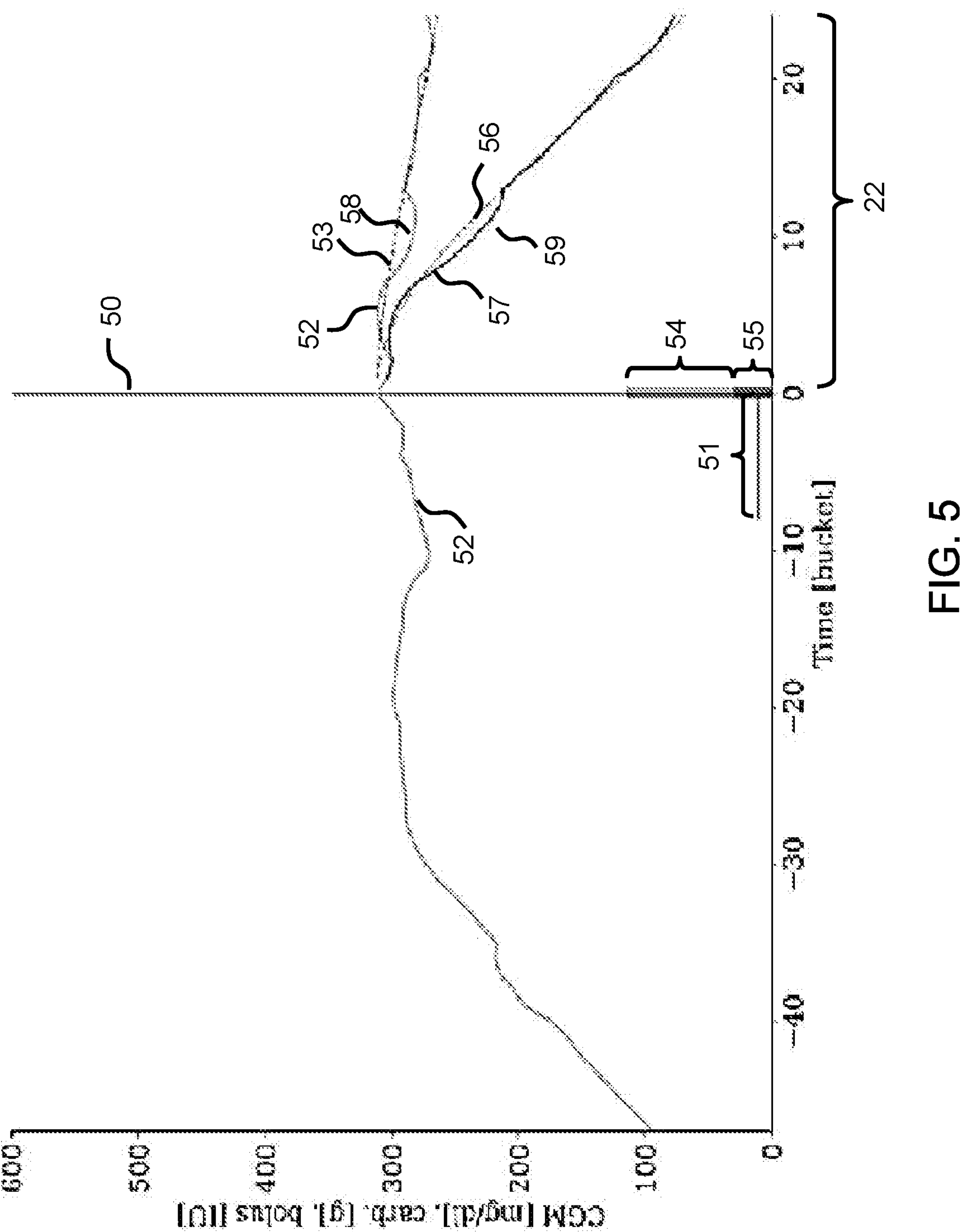
FIG. 5 is another graphical representation for generating an augmented CGM trace.

FIGS. 4 and 5 show graphical representations for generating an augmented CGM trace. The x-axis is scaled in time buckets before or after cutoff time 40, 50. Correspondingly, the last entry bucket of meal time window 41, 51 has time bucket value 0. CGM traces 42, 52 comprise actual/measured CGM values. Based on the last entry bucket of each meal time window 41, 51, a physiologically predicted trace 43, 53 is determined using a physiological model. Prediction takes place for the prediction time period 22. The differences between the actual CGM values in the CGM trace 42, 52 and the CGM values in the predicted trace 43, 53 are computed and stored in a residual CGM trace (not shown).

At the last entry bucket of meal time window 41, 51, values for taken carbohydrates and bolus insulin are replaced by an artificially (e.g., randomly) generated carbohydrate amount 44, 54 and bolus insulin amount 45, 55. Based on the artificially generated values 44, 45 (respectively 54, 55), a physiologically predicted artificial trace 46, 56 is determined using the physiological model. By adding the stored residual CGM trace to the artificial trace 46, 56, an augmented CGM trace 47, 57 is determined. Certain characteristics of the original CGM trace 42, 52 such as bumps 48, 58 can appear again (as bumps 49, 59) in the augmented CGM trace 47, 57.

Based on the described data augmentation approach, additional (augmented) training sets are constructed and employed for modelling. For all data augmentation methods, the datasets of the TEST partition are not further modified (i.e., not augmented) in order to thus assess model performance on the true data distribution.

In a comparative data driven (DD) only approach, the TRAIN datasets are not further preprocessed and are used as is when training models. The TEST datasets are not preprocessed, either.

In a further comparative hybrid (H) approach, the following dataset preprocessing steps are carried out on the (not augmented) TRAIN and TEST datasets. A physiological model as defined above is employed and CGM residuals instead of (non-residual) CGM values are used as target variables for modelling. The CGM residuals are defined as follows:

$$CGM_{res,i} = CGM_{pred\_phys,i} - CGM_{act,i}, \quad \text{(Eq. 9)}$$

where $CGM_{res,\ i}$ denotes the residual at the $i^{th}$ time point in units of mg/dl, $CGM_{\ pred\_phys,\ i}$ denotes the $i^{th}$ predicted CGM value by the physiological model in units of mg/dl, and $CGM_{act,\ i}$ denotes the $i^{th}$ actual CGM value in units of mg/dl. The predictions in CGM residual space are transformed back into CGM space, when evaluating the model and comparing to other models.

Modelling

After preprocessing the datasets DS, the (software-implemented) machine learning models are trained based on a sequence-to-sequence modelling architecture. As input, the machine learning models require the preprocessed datasets DS established with the data augmentation (DDwDA) approach, the data driven (DD) only approach, or the hybrid (H) approach.

For modelling, a scaling function for scaling the dataset can be employed, e.g., MinMax. The features of the dataset may, e.g., be scaled to the interval [−1, 1].

Figure 6:
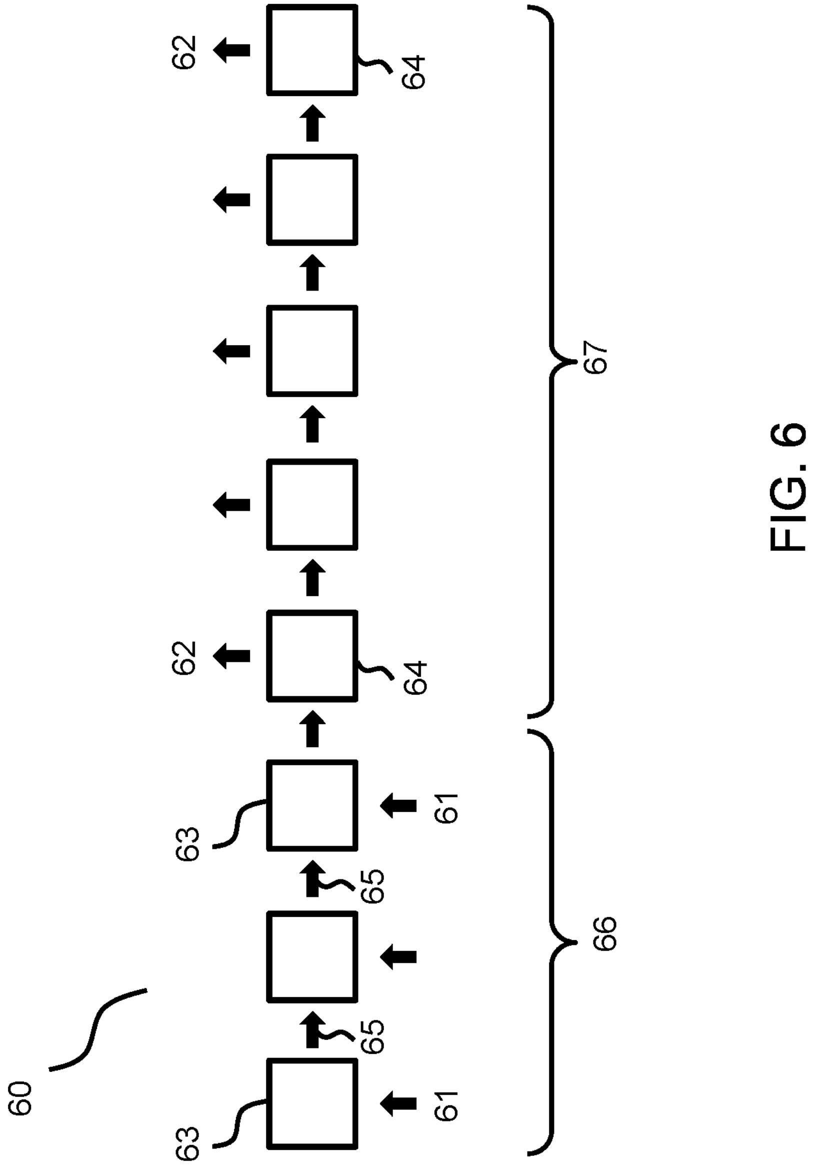
FIG. 6 is a graphical representation of an encoder-decoder recurrent neural network.

FIG. 6 shows a graphical representation of an encoder-decoder recurrent neural network (ED-RNN) 60, with which the machine learning model is trained. The ED-RNN 60 takes a plurality (sequence) of input values 61 and yields a plurality (sequence) of output values 62. This corresponds to a many-to-many architecture. A certain number of encoder cells 63, each taking one input value 61, are followed by a number of decoder cells 64, each producing one output value 62. The cells 63, 64 are arranged in a chain and each of the cells 63, 64 (except for the last cell) produces a state 65 as input for the next cell in the chain. The encoder cells 63 belong to a first phase 66 and the decoder cells 62 belong to a second phase 67.

Variable prediction time windows (PTW) and feature extraction time windows (FETW) can be used. The ED-RNN 60 is characterized by the following hyperparameters, which can be optimized:

- number of layers, representing the depth of the network,
- number of nodes, representing the width in a specific layer,
- type of the cells 64, 65 (long short-term memory (LSTM) or gated recurrent unit (GRU)),
- learning rate (step size), the speed at which weights are overwritten after each iteration,
- batch size, the number of training samples utilized in one iteration.
- number of epochs, the number of times that the learning algorithm will work through the entire training dataset DS,
- loss function, the function used to calculate the cost of errors (e.g., mean square error),
- optimizer, the optimization algorithm used by the algorithm (e.g., ADAM),
- regularizer, the type of technique used to avoid overfitting, and
- regularizer factor, the coefficient factor applied with the regularizer.

It can be provided that at least some of the hyperparameters are optimized during modelling. Alternatively, all hyperparameters are fixed. For example, the number of layers can be 128, 256, or 512. The batch size can be 128, 256, or 512. The number of epochs can be any integer between 1 and 20, preferably 5 or 7. The learning rate can be between $10^{-4}$ and $10^{-1}$, preferably $10^{-3}$.

Instead of an ED-RNN, other types of artificial neural networks can also be used for modelling.

Evaluation and Results

The prediction performance of the established machine learning model is evaluated using the TEST data sets comprising input variables $X_{test}$ and output variables $y_{test}$.

For evaluation, the prediction values are unscaled. The prediction performance is evaluated in (non-residual) CGM space. In case of the hybrid approach, the target variable values $CGM_{res,i}$ have therefore to be transformed back to non-residual CGM values beforehand.

Subsequently, the prediction values are evaluated by use of a metric. The following metrics can be employed to evaluate the machine learning models:

- accuracy and
- sensitivity towards bolus insulin and/or carbohydrates.

The accuracy corresponds to a percentage of CGM prediction values within +/−15% (or 15 mg/dl) of true CGM values above or equal 100 mg/dl (below 100 mg/dl) at corresponding points in time. The sensitivity towards bolus insulin and/or carbohydrates corresponds to a degree of change in predicted CGM (in mg/dl per unit of insulin). At the cutoff, a small change in insulin, ΔI, or carbohydrates, ΔCarb is added to the corresponding values. From this follows a change in CGM prediction, dCGM, for each time. Hence if dCGM(t)=ƒ (ΔI) then Sensitivity=dCGM(t)/ΔI; and if dCGM(t)=ƒ(ΔCarb) then Sensitivity=dCGM(t)/ΔCarb.

Sensitivity here means the average sensitivity at t=90 minutes.

The evaluation metrics are computed separately for every prediction time point. All samples for a particular prediction time are aggregated, e.g., by using a median.

For each approach (DD, DDwDA, H), the machine learning model with the highest mean accuracy over 120 minutes on the general scenario was selected. The results are summarized in the following.

| | Data-Driven (DD) | | Data-driven with Data Augmentation (DDwDA) | | Hybrid (H) | |
|---|---|---|---|---|---|---|
| Pre-Processed Dataset | data augmentation parameters: N/A target: CGM | | data augmentation parameters: max_carbohydrates = 250 g, max_bolus_insulin = 40 IU, max_cgm = 1200 mg/dl, min_cgm = −400 mg/dl, mtw = 45 min, data_multiplier = 1.05, replace_original_data = false, only_augment_samples_with_event_at_cutoff = true, augmentation_in_ACDE = false target: CGM | | data augmentation parameters: N/A target: Residual CGM | |
| Modelling Parameters | scale: minmax, scale target: true, layers: [256], cell: GRU, LR: 0.001, batch: 256, epochs: 5 | | scale: minmax, scale target: true, layers: [256], cell: GRU, LR: 0.001, batch: 256, epochs: 7 | | scale: minmax, scale target: true, layers: [256], cell: GRU, LR: 0.001, batch: 256, epochs: 5 | |
| Scenario | general | postprandial | general | postprandial | general | postprandial |
| Mean Accuracy Over 120 min [%] | 65.2 | 55.5 | 63.3 | 52.6 | 62.0 | 51.4 |
| Median Bolus Sensitivity at 90 min [(mg/dl)/IU] | 0.1 | 0.1 | −9.0 | −9.9 | −17.4 | −16.8 |

Figure 7:
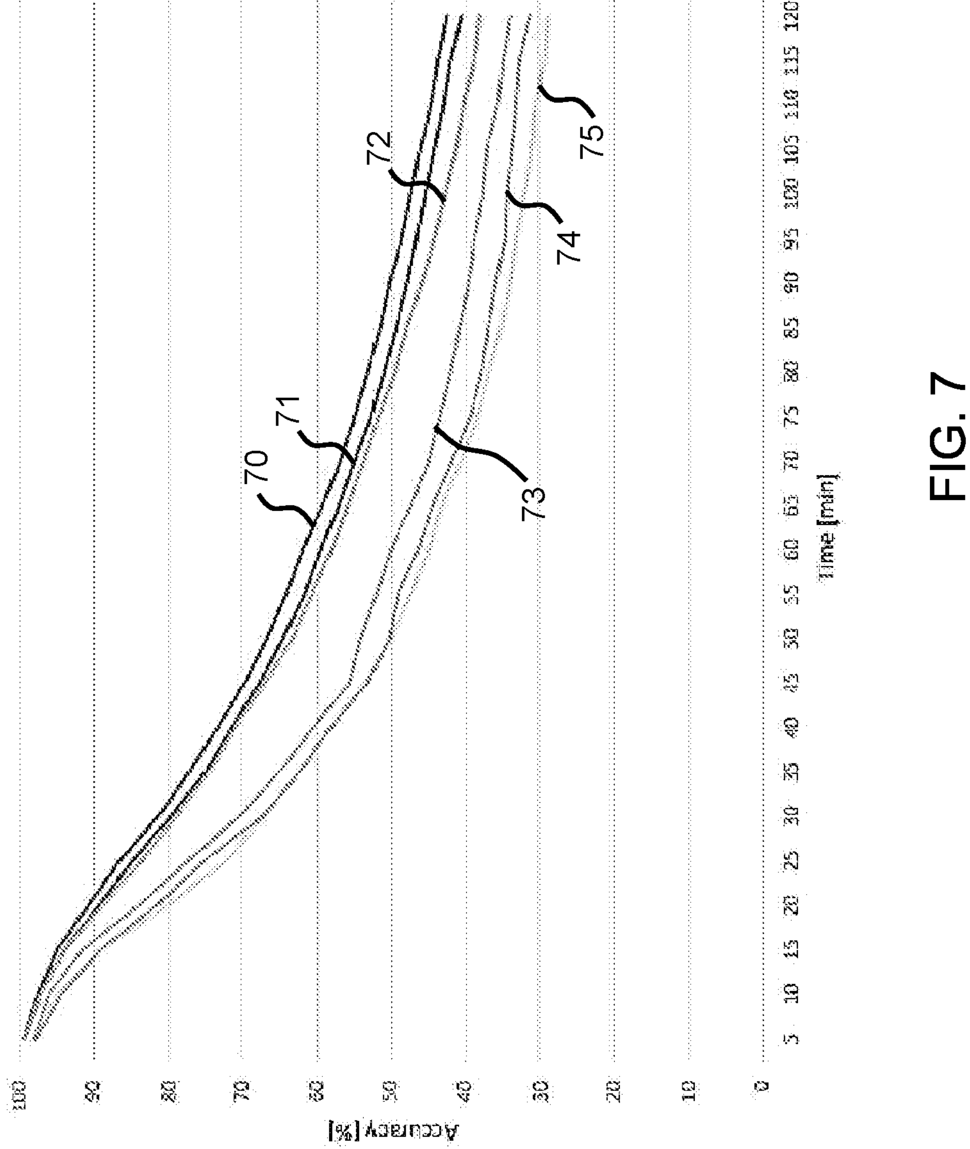
FIG. 7 is a graphical representation for accuracy as a function of time for in a general and a postprandial scenario.

FIG. 7 shows a graphical representation for accuracy (in %) as a function of time (in minutes) for the DD, the DDwDA, and the H approach in the general and the postprandial scenario.

Lines 70, 71, and 72 represent the accuracy values for the DD, the DDwDA, and the H approach, respectively, in the general scenario, and lines 73, 74, and 75 represent the accuracy values for the DD, the DDwDA, and the H approach, respectively, in the postprandial scenario. All accuracy values decrease monotonously with time. The accuracy values for the DD approach are highest in both scenarios, while the accuracy values for the H approach are the lowest in both scenarios for most times. Hence, by adding artificial data, a higher sensitivity is achieved, but performance may be decreased.

Figure 8:
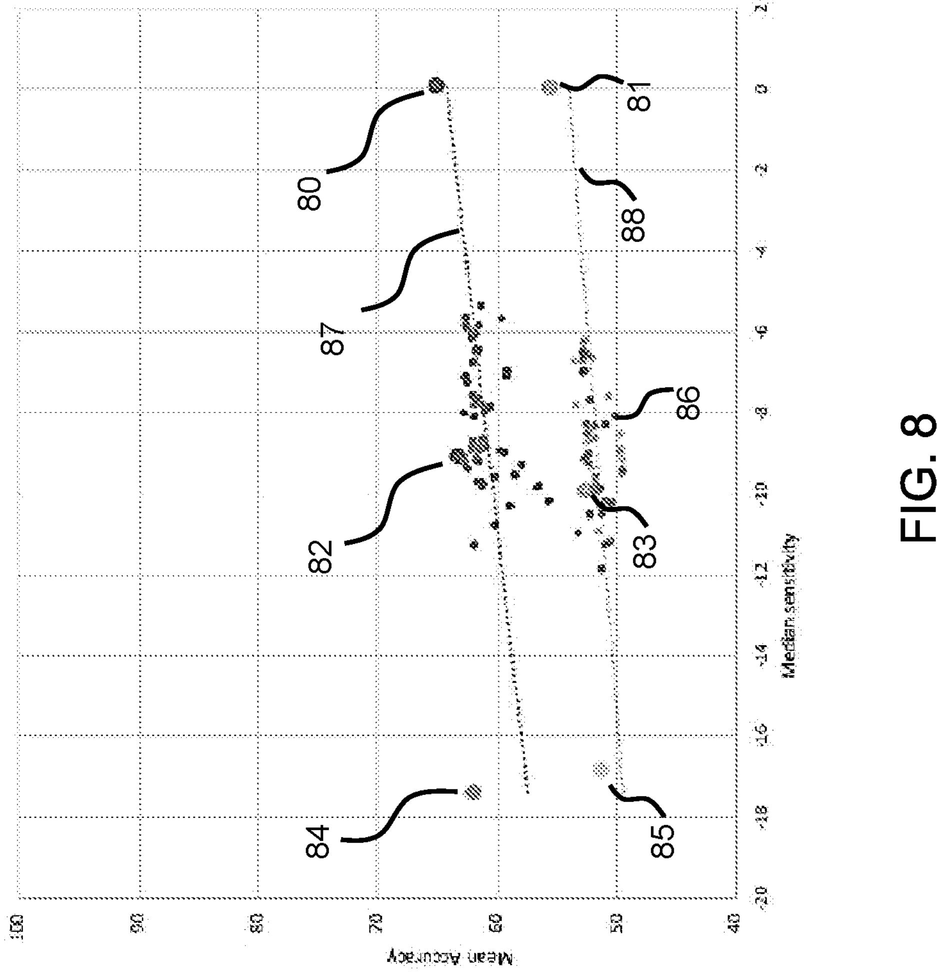
FIG. 8 is a graphical representation for the mean accuracy as a function of model sensitivity towards insulin.

FIG. 8 shows a graphical representation for the mean accuracy (in %) over 120 minutes as a function of model sensitivity towards insulin (in (mg/dl)/IU). Results from each of the three approaches (DD general 80, DD postprandial 81, DDwDA general 82, DDwDA postprandial 83, H general 84, H postprandial 85) as well as further data 86 driven with data augmentation models are displayed. The further data 86 were created are using the same data augmentation technique, but with different parameters and/hyperparameters. Lines 87 and 88 represent linear fits of the DDwDA data points in the general and the postprandial scenario, respectively.

The DDwDA model represented by data points 82, 83 constitutes the best DDwDA model in terms of accuracy over 120 minutes in the general scenario.

The features disclosed in this specification, the figures and/or the claims may be material for the realization of various embodiments, taken in isolation or in various combinations thereof.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method for generating a software-implemented module for use in a glucose monitoring system to determine a glucose value in a body fluid, the method comprising:

(A) providing a first set of input data indicative of first values measured for a first input parameter and a second input parameter, wherein the first input parameter and/or the second input parameter is selected from the group of input parameters consisting of: glucose level measured by a continuous glucose sensor, insulin bolus, carbohydrate intake, active bolus insulin, active basal insulin, activity level, insulin sensitivity factor, carbohydrate ratio, stress level, and glycemic index of carbohydrates;

(B) providing a second set of input data indicative of second values for the first and second input parameters, the second values comprising:

(i) an augmented value for the first parameter, the augmented value being different from the first value measured for the first input parameter, and (ii) the first value for the second input parameter;

(C) determining first analyte data indicative of a first set of glucose values in a body fluid by processing the first set of input data from Step (A) by a physiological model;

(D) determining second analyte data indicative of a second set of glucose values by processing the second set of input data from Step (B) by the physiological model;

(E) determining a set of training data from both the first analyte data and the second analyte data;

(F) determining a set of test data different from the set of training data;

(G) providing a software-implemented machine learning model configured to determine a glucose value in a body fluid of a patient;

(H) training the software-implemented machine learning model by the set of training data;

(I) testing the software-implemented machine learning model by the set of test data;

(J) deploying the generated software implemented module for use in the glucose monitoring system to analyze a present input data and determine an analyte value, wherein the analyte value is a present analyte value and/or a future analyte value.

2. The method of claim 1, wherein: determining of the first analyte data comprises determining first predictive analyte data indicative of a first time dependent course of the analyte values for the analyte over a prediction time period by processing the first set of input data by the physiological model; and determining of the second analyte data comprises determining second predictive analyte data indicative of a second time dependent course of the analyte values for the analyte over the prediction time period by processing the second set of input data by the physiological model.

3. The method of claim 2, wherein the prediction time period is provided as a continuation of the measurement time period.

4. The method of claim 1, wherein: providing of the first set of input data comprises providing a first set of input data indicative of first values measured for the first and second input parameters over a measurement time period; and providing of the second set of input data comprises providing a second set of input data indicative of second values for the first and second the input parameters over the measurement time period.

5. The method of claim 1, further comprising: receiving limit data indicative of a parameter limit for the first input parameter; and limiting augmenting of the first value for the first input parameter.

6. The method of claim 1, wherein determining of the set of test data comprises determining a set of test data from the first analyte data only.

7. The method of claim 1, wherein determining of the set of training data comprises: determining residual analyte data; determining augmented analyte data from the second analyte data and the residual analyte data; and determining the set of training data at least from the augmented analyte data.

8. The method of claim 7, wherein the determining of the residual analyte data comprises determining residual analyte data from the first analyte data and measured analyte data.

9. The method of claim 1, wherein providing of the first set of input data comprises providing a first set of continuous input data indicative of first values continuously measured for a plurality of input parameters.

10. The method of claim 1, further comprising: providing a third set of input data indicative of third values of input parameters, the third values comprising (i) an augmented value for at least one other input parameter from the first and second of input parameters, the augmented value being different from the first value measured for the at least one other input parameter and determined by augmenting the first value, and (ii) the first value for at least one remaining input parameter; determining third analyte data indicative of a third plurality of analyte values for the analyte by processing the third set of input data by the physiological model; and determining a set of training data from the first analyte data, the second analyte data, and the third analyte data.

11. A non-transitory computer readable medium having stored thereon computer-executable instructions for performing the method according to claim 1.

12. A method for determining a glucose value in a body fluid, comprising, in an arrangement of one or more data processors: providing a software-implemented module generated by the method according to claim 1; providing present input data indicative of present values measured for a plurality of input parameters for a fluid containing an analyte being glucose in a body fluid; and determining a glucose value in a body fluid of a patient comprising analyzing the present input data by the software-implemented module.

13. The method of claim 12, further comprising at least one of: outputting the analyte value to the patient through an output device; and if the glucose value is below a minimum threshold or above a maximum threshold, outputting an alarm to the patient.

14. A system for determining a glucose value in a body fluid, the system having an arrangement of one or more data processors and a software-implemented module generated by the method according to claim 1, wherein the one or more data processors are configured to: provide present input data indicative of present values measured for a plurality of input parameters for a body fluid containing glucose; and determine a glucose value by analyzing the present input data by the software-implemented module.

15. A system for generating a software-implemented module for use in a glucose monitoring system to determine a glucose value in a body fluid, the system comprising an arrangement of one or more data processors, wherein the one or more processors are configured to:

(A) provide a first set of input data indicative of first values measured for a first input parameter and a second input parameter, wherein the first input parameter and/or the second input parameter is selected from the group of input parameters consisting of: glucose level measured by a continuous glucose sensor, insulin bolus, carbohydrate intake, active bolus insulin, active basal insulin, activity level, insulin sensitivity factor, carbohydrate ratio, stress level, and glycemic index of carbohydrates;

(B) provide a second set of input data indicative of second values for the first and second input parameters, the second values comprising (i) an augmented value for the first parameter, the augmented value being different from the first value measured for the first input parameter, and (ii) the first value for the second input parameter;

(C) determine first analyte data indicative of a first set of glucose values in a body fluid by processing the first set of input data from (A) by a physiological model;

(D) determine second analyte data indicative of a second set of glucose values by processing the second set of input data from (B) by the physiological model;

(E) determine a set of training data from both the first analyte data and the second analyte data;

(F) determine a set of test data different from the set of training data;

(G) provide a software-implemented machine learning model configured to determine a glucose value in a body fluid of a patient;

(H) train the software-implemented machine learning model by the set of training data;

(I) test the software-implemented machine learning model by the set of test data; and (J) deploy the generated software implemented module for use in the glucose monitoring system to analyze a present input data and determine an analyte value, wherein the analyte value is a present analyte value and/or a future analyte value.

* * * * *